US00PP34409P2

(12) United States Plant Patent
Post

(10) Patent No.: US PP34,409 P2
(45) Date of Patent: Jul. 5, 2022

(54) ***CHRYSANTHEMUM* PLANT NAMED 'DLFALEM5'**

(50) Latin Name: ***Chrysanthemum* X *morifolium***
Varietal Denomination: 'DLFALEM5'

(71) Applicant: Arie Gerard Post, Delft (NL)

(72) Inventor: Arie Gerard Post, Delft (NL)

(73) Assignee: DELIFLOR ROYALTIES B.V., Maasdijk (NL)

( * ) Notice: Subject to any disclaimer, the term of this patent is extended or adjusted under 35 U.S.C. 154(b) by 0 days.

(21) Appl. No.: 17/548,555

(22) Filed: Dec. 12, 2021

Related U.S. Application Data

(60) Provisional application No. 63/124,834, filed on Dec. 13, 2020.

(51) Int. Cl.
*A01H 5/02* (2018.01)
*A01H 6/14* (2018.01)

(52) U.S. Cl.
USPC ..... Plt./287

(58) Field of Classification Search
USPC ..... Plt./284, 286, 287
See application file for complete search history.

*Primary Examiner* — Susan McCormick Ewoldt
(74) *Attorney, Agent, or Firm* — C. Anne Whealy

(57) ABSTRACT

A new and distinct cultivar of *Chrysanthemum* plant named 'DLFALEM5', characterized by its upright plant habit; uniform growth habit; vigorous growth habit; durable dark green-colored leaves; strong upright flowering stems; pom-pon-type inflorescences with bright yellow green-colored incurved ray florets; relatively tolerant to low production temperatures; and good postproduction longevity.

1 Drawing Sheet

Figure 1:
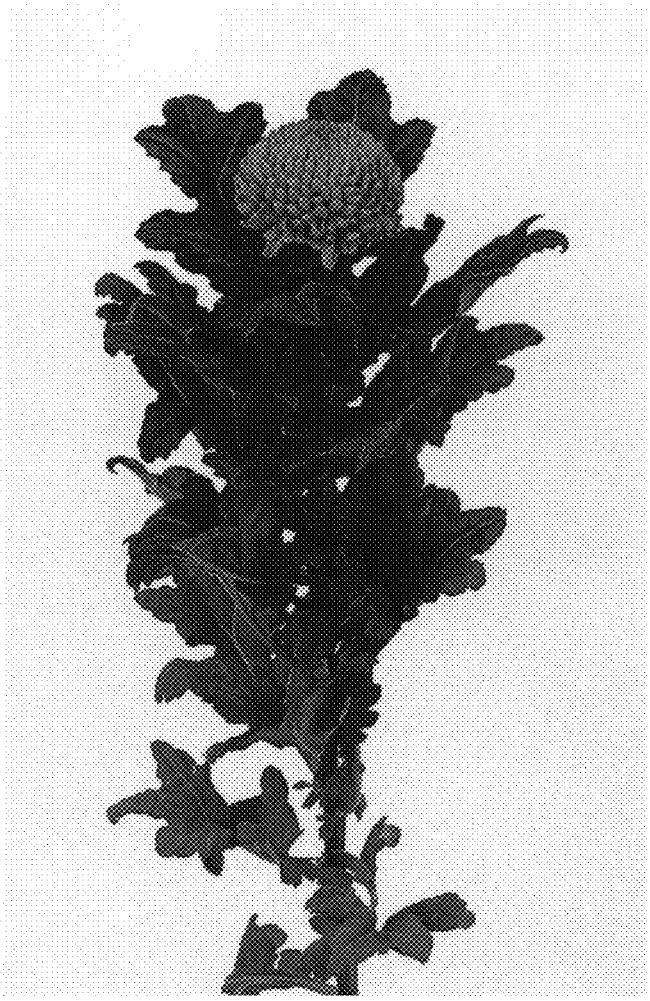

Botanical designation: *Chrysanthemum* X *morifolium*.
Cultivar denomination: 'DLFALEM5'.

STATEMENT REGARDING PRIOR DISCLOSURES BY INVENTOR/APPLICANT & ASSIGNEE

A Columbian Plant Breeder's Rights application for the instant plant was filed by the Assignee, Deliflor Royalties B.V. of Maasdijk, The Netherlands on Dec. 29, 2020, application number A202736. Foreign priority is not claimed to this application.

The Inventor/Applicant and Assignee assert that no publications nor advertisements relating to sales, offers for sale or public distribution occurred more than one year prior to the effective filing date of this application. Any information about the claimed plant would have been obtained from a direct or indirect disclosure from the Inventor/Applicant and/or the Assignee. Inventor/Applicant and Assignee claim a prior art exception under 35 U.S.C. 102(b)(1) for disclosure and/or sales prior to the filing date but less than one year prior to the effective filing date.

BACKGROUND OF THE INVENTION

The present invention relates to a new and distinct cultivar of *Chrysanthemum* plant, botanically known as *Chrysanthemum* x *morifolium*, typically grown as a cut flower *Chrysanthemum* and hereinafter referred to by the name 'DLFALEM5'.

The new *Chrysanthemum* plant is a product of a planned breeding program conducted by the Inventor in Maasdijk, The Netherlands. The objective of the breeding program is to create new cut flower *Chrysanthemum* plants with unique and attractive inflorescences.

The new *Chrysanthemum* plant originated from a cross-pollination in October, 2017 of a proprietary selection of *Chrysanthemum* x *morifolium* identified as code number db 10874, not patented, as the female, or seed, parent with a proprietary selection of *Chrysanthemum* x *morifolium* identified as code number db 10131, not patented, as the male, or pollen, parent. The new *Chrysanthemum* plant was discovered and selected as a single flowering plant from within the progeny of the stated cross-pollination in a controlled greenhouse environment in Maasdijk, The Netherlands in October, 2018.

Asexual reproduction of the new *Chrysanthemum* plant by vegetative terminal cuttings since October, 2018 in a controlled greenhouse environment in Maasdijk, The Netherlands, has shown that the unique features of this new *Chrysanthemum* plant are stable and reproduced true to type in successive generations of asexual reproduction.

SUMMARY OF THE INVENTION

Plants of the new *Chrysanthemum* have not been observed under all possible combinations of environmental conditions and cultural practices. The phenotype may vary somewhat with variations in environmental conditions such as temperature, daylength and light intensity, without, however, any variance in genotype.

The following traits have been repeatedly observed and are determined to be the unique characteristics of 'DLFALEM5'. These characteristics in combination distinguish 'DLFALEM5' as a new and distinct *Chrysanthemum* plant:

1. Upright plant habit; uniform growth habit.
2. Vigorous growth habit.
3. Durable dark green-colored leaves.
4. Strong upright flowering stems.

5. Pompon-type inflorescences with bright yellow green-colored incurved ray florets.
6. Relatively tolerant to low production temperatures.
7. Good postproduction longevity.

Plants of the new *Chrysanthemum* differ primarily from plants of the female parent selection in ray floret aspect and shape as ray florets of plants of the new *Chrysanthemum* are moderately concave and have retuse to emarginate apices whereas ray florets of plants of the female parent selection are slightly concave and have rounded apices.

Plants of the new *Chrysanthemum* differ primarily from plants of the male parent selection in inflorescence size and ray floret shape as ray plants of the new *Chrysanthemum* have smaller inflorescences with oblanceolate to narrowly oblong incurved ray florets whereas plants of the male parent selection have larger inflorescences with quilled ray florets.

Plants of the new *Chrysanthemum* can be compared to plants of *Chrysanthemum* X *morifolium* 'Delirubino', not patented. In side-by-side comparisons, plants of the new *Chrysanthemum* differ primarily from plants of 'Delirubino' in ray floret color as ray florets of plants of the new *Chrysanthemum* are darker yellow green in than ray florets of plants of 'Delirubino'. In addition, ray florets of plants of the new *Chrysanthemum* are incurved whereas ray florets of plants of 'Delirubino' are not incurved.

BRIEF DESCRIPTION OF THE PHOTOGRAPHS

The accompanying photographs illustrate the overall appearance of the new *Chrysanthemum* plant showing the colors as true as it is reasonably possible to obtain in colored reproductions of this type.

The photograph at the top of the sheet (FIG. 1) comprises a side perspective view of a typical flowering stem of 'DLFALEM5' grown as a disbud-type cut flower.

Figure 2:
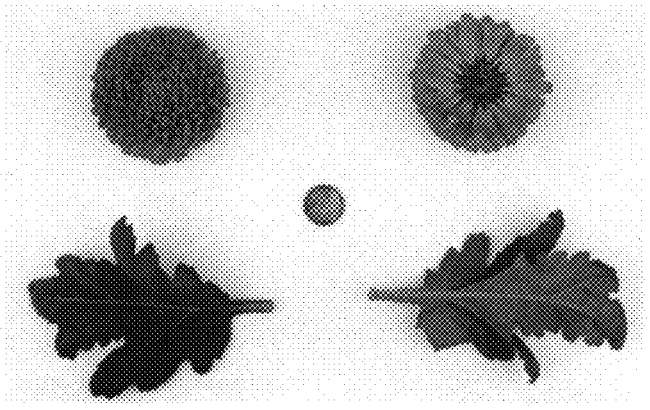

The photograph at the bottom of the sheet (FIG. 2) is a close-up view of upper (left) and lower (right) surfaces of typical inflorescences and typical leaves of 'DLFALEM5'.

DETAILED BOTANICAL DESCRIPTION

The aforementioned photographs and following observations and measurements describe plants grown during the late winter in ground beds in a glass-covered greenhouse in Maasdijk, The Netherlands and under cultural practices typical of commercial cut *Chrysanthemum* production. Plants were initially given long day/short night treatments followed by short day/long night treatments to induce flower initiation and development. During the production of the plants, day temperatures ranged from 18° C. to 25° C., night temperatures ranged from 20° C. to 22° C. and light levels averaged 7 klux. Plants were grown as single-stem disbud-type plants and were ten weeks old when the photographs and the description were taken. In the following description, color references are made to The Royal Horticultural Society Colour Chart, 2015 Edition, except where general terms of ordinary dictionary significance are used.

Botanical classification: *Chrysanthemum* X *morifolium* 'DLFALEM5'.

Parentage:

*Female, or seed, parent*.—Proprietary selection of *Chrysanthemum* x *morifolium* identified as code number db 10874, not patented.

*Male, or pollen, parent*.—Proprietary selection of *Chrysanthemum* x *morifolium* identified as code number db 10131, not patented.

Propagation:

*Type*.—Terminal vegetative cuttings.

*Time to initiate roots, summer*.—About four days at temperatures about 20° C.

*Time to initiate roots, winter*.—About six days at temperatures about 20° C.

*Time to produce a rooted young plant, summer*.—About 13 days at temperatures about 20° C.

*Time to produce a rooted young plant, winter*.—About 15 days at temperatures about 20° C.

*Root description*.—Fine, fibrous; typically creamy white in color, actual color of the roots is dependent on substrate composition, water quality, fertilizers, substrate temperature and physiological age of roots.

*Rooting habit*.—Freely branching, medium density.

Plant description:

*Plant and growth habit*.—Herbaceous pompon-type cut flower that is typically grown as a single stem disbud-type; upright plant habit; vigorous growth habit and rapid growth rate.

*Plant height, soil level to top of foliar plane*.—About 75 cm.

*Plant height, soil level to top of inflorescence plane*.—About 83.1 cm.

*Plant (spray) diameter*.—About 20.5 cm.

*Flowering stem length*.—About 70.8 cm.

*Flowering stem diameter*.—About 8 mm.

*Flowering stem internode length*.—About 2.6 cm.

*Flowering stem strength*.—Strong.

*Flowering stem aspect*.—Erect.

*Flowering stem texture and luster*.—Sparsely to moderately pubescent; slightly glossy.

*Flowering stem color, developing*.—Close to a blend of 144A and 146B.

*Flowering stem color, developed*.—Close to 146A to 146B; at the ridges, close to 148A.

*Leaf description*.—Arrangement: Alternate; simple. Length: About 12.3 cm. Width: About 9.1 cm. Shape, in overall outline: Broadly ovate to broadly elliptic. Apex: Abruptly acute. Base: Attenuate. Margin: Palmately lobed, coarsely dentate to serrate; sinuses convergent and medium to deep in depth; undulate. Texture and luster, upper surface: Moderately pubescent, not rugose; moderately velvety; slightly glossy. Texture and luster, lower surface: Moderately pubescent, prominent venation; slightly velvety; slightly glossy. Venation pattern: Pinnate, reticulate. Color: Developing leaves, upper surface: Close to 143A. Developing leaves, lower surface: Close to 138B. Fully developed leaves, upper surface: Close to a blend of NN137A and 147A; venation, close to 147B. Fully developed leaves, lower surface: Close to 147B; venation, close to 146B to 146C. Petioles: Length: About 3 cm. Diameter: About 3.5 mm by 6 mm. Strength: Moderately strong. Texture and luster, upper and lower surfaces: Moderately pubescent; slightly glossy. Color, upper surface: Close to 146A; edges, slightly darker than 137A. Color, lower surface: Close to 146B; edges, close to 147B. Stipules: Quantity and appearance: Two leafy stipules, opposite, at the petiole attachment to the stem. Length: About 1.4 cm. Width: About 2.9 cm. Shape, in overall outline: Roughly reniform or cleft into two or three lobes; apex, apiculate and incised; base, broadly cuneate. Texture and luster, upper and lower surfaces: Moderately pubescent; slightly glossy. Color, upper surface: Close to a blend of NN137A and 147A. Color, lower surface: Close to 147B.

Inflorescence description:

*Appearance*.—Pompon-type inflorescence form with incurved oblanceolate to narrowly oblong-shaped ray florets and tubular disc florets; inflorescences borne perpendicular to peduncles and face upright; ray and disc florets develop acropetally on a capitulum.

*Fragrance*.—Faintly fragrant; typical of *Chrysanthemums*.

*Flowering response*.—Under natural conditions, plant flower in the autumn/winter in the Northern Hemisphere; at other times of the year, inflorescence initiation and development can be induced under short day/long night conditions (at least 13.5 hours of darkness); uniform flowering habit and short response time, plants exposed to two weeks of long day/short night conditions after planting followed by photoinductive short day/long night conditions flower about 56 days later when grown as a disbud-type.

*Postproduction longevity*.—Good postproduction longevity; after a seven-day storage period, cut flowers will maintain good color and substance for about two weeks in an interior environment; inflorescences persistent.

*Quantity of inflorescences*.—Typically grown as a disbud-type, only the terminal inflorescence is allowed to developed; if grown as a spray-type, about 19 inflorescences develop per flowering stem.

*Inflorescence size*.—Diameter, grown as a disbud-type: About 8.8 cm. Depth (height), grown as a disbud-type: About 6.7 cm. Diameter, grown as a spray-type: About 6.7 cm. Depth (height), grown as a spray-type: About 2.5 cm. Disc diameter: About 6 mm.

*Receptacles*.—Height: About 5 mm. Diameter: About 1.6 cm. Shape: Flattened globular. Color: Close to 145C and 145D.

*Inflorescence buds*.—Height: About 1 cm. Diameter: About 1.8 cm. Shape: Flattened ovoid. Texture and luster: Moderately pubescent; slightly glossy. Color: Developing involucral bracts, close to 137A to 137B and 138A; developing ray florets, close to 145B to 145C.

*Ray florets*.—Quantity and arrangement: About 360 arranged in about twelve whorls. Length: About 3.3 cm, varying between 1.4 cm and 4.3 cm. Width: About 1 cm, varying between 0.3 cm and 1.5 cm. Shape: Oblanceolate to narrowly oblong; moderately concave and incurved. Apex: Retuse to emarginate. Base: Attenuate. Margin: Entire; not undulate. Aspect: About 60° from vertical. Texture and luster, upper surface: Smooth, glabrous; slightly velvety; slightly glossy. Texture and luster, lower surface: Sparsely pubescent; slightly velvety; slightly glossy. Color: When opening, upper surface: Close to 145A; towards the base, close to 144D. When opening, lower surface: Close to 144B; towards the base, close to 145C. Fully opened, upper surface: Close to a blend of 144B and 145A; towards the base, close to 145B; innermost ray florets, close to 154D with apices, close to 144B; venation, similar to lamina colors; color does not change with subsequent development. Fully opened, lower surface: Close to 144B; towards the base, close to 144C; innermost ray florets, close to 154D with apices, close to 144B; venation, similar to lamina colors; color does not change with subsequent development.

*Disc florets*.—Quantity and arrangement: About 15 randomly arranged at the center of the receptacle; disc florets typically do not completely develop. Length: About 8 mm. Diameter: About 1.25 mm. Shape: Tubular. Apex: Obtuse. Margin, free-part: Entire. Texture and luster, inner and outer surfaces: Smooth, glabrous; glossy. Color: Towards the apex, close to 144A; mid-section and towards the base, close to 1D; at the base, close to 145D.

*Involucral bracts*.—Quantity and arrangement: About 38 arranged in about two whorls. Length: About 1 cm. Width: About 4 mm. Shape: Narrowly oblong to narrowly ovate. Apex: Bluntly acute. Base: Cuneate. Margin: Entire. Texture and luster, upper surface: Smooth, glabrous; glossy. Texture and luster, lower surface: Moderately pubescent; matte. Color, upper surface: Close to 146A to 146B; lateral margins, translucent and close to 157C and apical margins tinged with close to N199A. Color, lower surface: Close to 137A and 137B; lateral margins, translucent and close to 157C and apical margins tinged with close to N199A.

*Peduncles*.—Length, terminal peduncle: About 8.6 cm. Diameter, terminal peduncle: About 5.5 mm. Length, third peduncle, grown as a spray-type: About 12.7 cm. Diameter, third peduncle, grown as a spray-type: About 3.5 mm. Strength: Strong. Aspect, terminal peduncle: Upright. Aspect, third peduncle, grown as a spray-type: About 30° from the flowering stem axis. Texture and luster: Moderately pubescent; moderately glossy. Color: Close to 146A; at the ridges, close to between 146A and 146B.

*Reproductive organs*.—Androecium: To date, stamen development has not been observed on plants of the new *Chrysanthemum*. Gynoecium: Present only on ray florets as disc florets do not fully develop. Quantity: One per floret. Pistil length: About 8 mm. Style length: About 7 mm. Style color: Close to 145C. Stigma diameter: About 1.5 mm. Stigma shape: Cleft, decurrent. Stigma color: Close to 154C. Ovary color: Close to 157D.

*Seeds and fruits*.—To date, seed and fruit development have not been observed on plants of the new *Chrysanthemum*.

Pathogen & pest resistance: To date, plants of the new *Chrysanthemum* have not been observed to be resistant to pathogens and pests common to *Chrysanthemum* plants grown under commercial conditions.

Temperature tolerance: Plants of the new *Chrysanthemum* have been observed to tolerate temperatures ranging from about −12° C. to 35° C. and to be suitable for USDA Hardiness Zones 8 to 10.

It is claimed:

1. A new and distinct *Chrysanthemum* plant named 'DLFALEM5' as illustrated and described.

* * * * *